United States Patent [19]
Charles et al.

[11] 4,116,775
[45] Sep. 26, 1978

[54] MACHINE AND PROCESS FOR READING CARDS CONTAINING MEDICAL SPECIMENS

[75] Inventors: Ronald A. Charles, St. Louis County; Paul W. Jones, St. Charles; John L. Staples, Florissant; Joseph R. Wiegner, Ballwin, all of Mo.

[73] Assignee: McDonnell Douglas Corporation, St. Louis, Mo.

[21] Appl. No.: 682,728

[22] Filed: May 3, 1976

[51] Int. Cl.$^2$ .............................................. C12K 1/04
[52] U.S. Cl. ......................... 195/103.5 M; 23/230 B; 195/103.5 K; 195/127; 356/104
[58] Field of Search ................. 195/103.5 R, 103.5 K, 195/103.5 M, 127, 139; 23/230 B; 356/104

[56] References Cited
U.S. PATENT DOCUMENTS

| | | | |
|---|---|---|---|
| 3,493,772 | 2/1970 | Daughters et al. | 195/103.5 M |
| 3,725,204 | 4/1973 | Marshall, Jr. et al. | 195/127 |
| 3,736,432 | 5/1973 | Sweet | 195/103.5 M |
| 3,776,817 | 12/1973 | Van Der Pfordten | 195/103.5 K |
| 3,925,166 | 12/1975 | Blume | 195/139 |

*Primary Examiner*—Alvin E. Tanenholtz
*Assistant Examiner*—Robert J. Warden
*Attorney, Agent, or Firm*—Gravely, Lieder & Woodruff

[57] ABSTRACT

Medical specimens suspected of containing certain microorganisms are introduced into cards containing wells having culture media therein. A reduction in the light transmitting characteristics of any well indicates the presence of a microorganism. Each well is examined at periodic intervals by projecting a light through it. This light is monitored by a plurality of detectors located beyond, but nevertheless, in alignment with the well, and each detector provides a signal which is proportional to the intensity of the light cast upon it. If a detector registers an unduly large decrease in light transmission, whereas others associated with the same emitter do not, this probably indicates the presence of a bubble in the well, and the unduly large decrease is ignored. This enables the machine to look around bubbles. Adjustments are made for the change in light transmission caused by distortion of the flexible walls at the ends of the wells. Each card has identification segments which are composed of different bars, and each bar is read by an emitter which projects light through it and a plurality of detectors which are illuminated by the emitter, unless the bar is blocked out with a marking. A predetermined number of the detectors must register a light intensity above a prescribed threshold value to establish the absence of a marking in the bar which is read, and this enables the machine to disregard stray marks and foreign particles on the card. The card is moved incrementally through a reading head as the viewing wells and identification segments on it are read.

25 Claims, 17 Drawing Figures

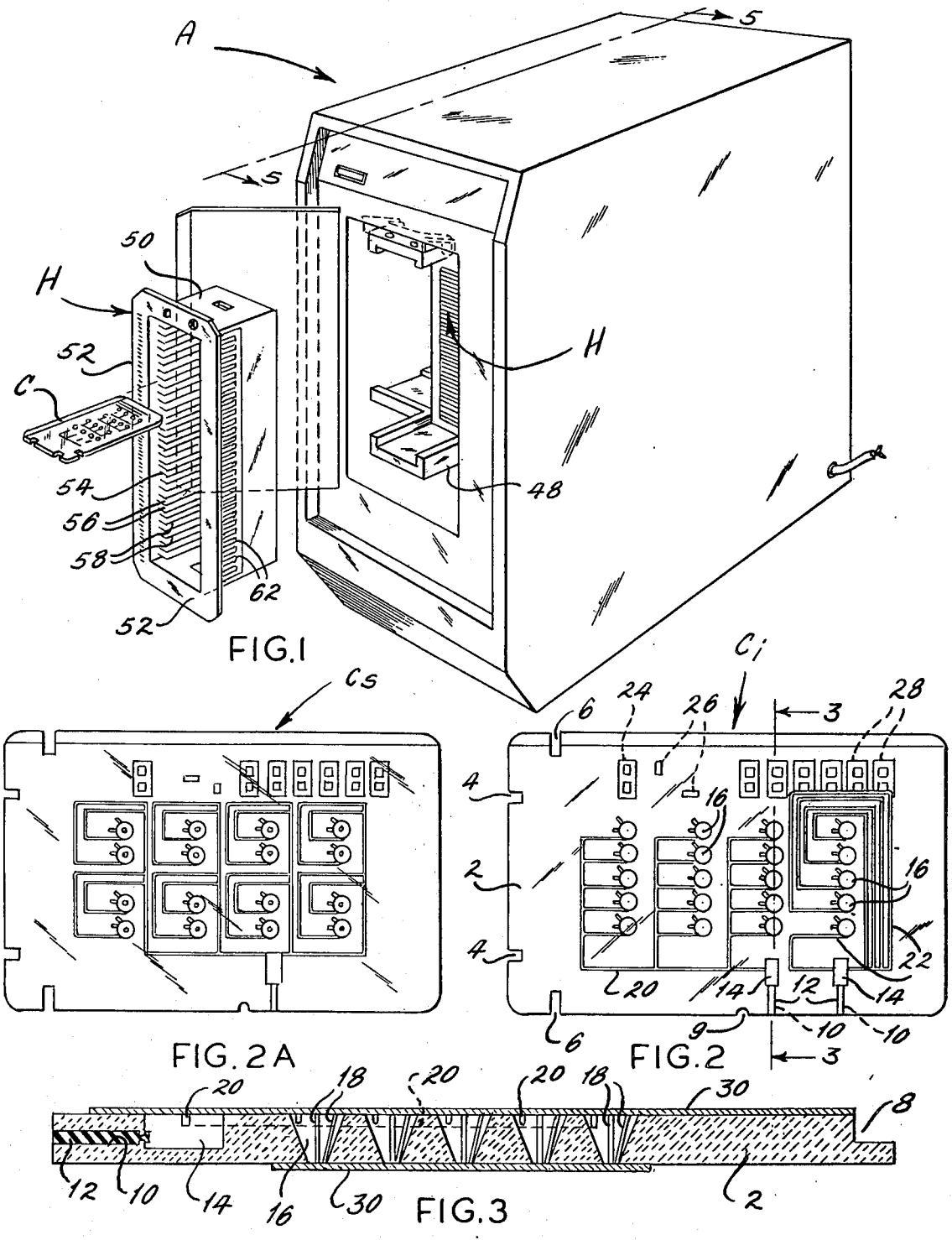

MACHINE AND PROCESS FOR READING CARDS CONTAINING MEDICAL SPECIMENS

BACKGROUND OF THE INVENTION

This invention relates in general to the detection of microorganisms and more particularly to a process and machine reading cards into which specimens suspected of containing microorganisms are introduced.

A procedure which has recently been developed for detecting the presence of microorganisms in specimens, and this procedure utilizes cards or cuvettes having wells filled with dehydrated culture media of a highly selective nature. Clinical specimens are diluted in saline solution and the dilutions so formed are introduced into the cards where they mix with and rehydrate the selective media in the wells. Each medium is selective in that it is specific to a particular microorganism, and when that microorganism metabolizes in the rehydrated medium, the medium undergoes an optical change. This change is usually characterized by an increase in turbidity or an alteration of color, and is detected by projecting light through the well containing the rehydrated medium and measuring the intensity of the light beyond the well. By mixing antibiotics with the media, it is possible to determine the susceptibility of an identified microorganism to various antibiotics, for if any antibiotic is effective, the culture medium in which it is present will retain substantially its original optical characteristics.

The foregoing procedure in an elementary form is disclosed in U.S. patent application Ser. No. 461,249 of C. Aldridge et al, filed Apr. 16, 1974, now U.S. Pat. No. 3,963,355, which further discloses several selective media which are suitable for use in this invention. U.S. patent application Ser. No. 528,840 of S. Gibson, et al, filed Dec. 2, 1974, discloses a card suitable for conducting antibiotic susceptibility tests. The U.S. patent application Ser. No. 682,664 of Ronald A. Charles, et al, filed May 3, 1976, and entitled AUTOMATED ANTIMICROBIAL ANALYZER discloses a machine for examining the wells of the cards on a high speed automated base.

Each card, in addition to its wells containing the selective media, has indicia marked upon it for identification purposes. This indicia, which for the most part is in the form of Arabic numerals, may be machine read by projecting light through the card. The interruption of any beam of light indicates the presence of a marking. Particles of foreign matter sometimes accumulate on the card at the identification segments, and these particles will block some light and consequently may provide false readings. Stray marking may also result in false readings.

The wells of the cards and the filling channels leading to them are isolated from the surrounding atmosphere. Each card is loaded with the diluted specimen by evacuating air from its interior and then replacing the evacuated air with the diluted specimen. A small volume of air usually remains in the card and this entrapped air may accumulate as a bubble in one or more of the wells. Bubbles, however, appear opaque to the automated reading apparatus and hence may indicate metabolic activity where none is present. Also, some microorganisms produce gas as they metabolize, and this gas will result a bubble which renders at deceptive reading as to the light transmitting characteristics of the rehydrated medium.

Also, it is not uncommon for the tape which covers the ends of the wells to bulge outwardly into a convex configuration as the card is incubated at elevated temperatures, and this alters the optical properties of the column through which the light is projected, thereby providing another basis for error. This bulging is in part attributable to the expansion resulting from the increase in temperature and in part to the natural production of gases resulting from the metabolic activity of some microorganisms. In any event, the bulging, or lensing as it is called, takes place over a period of about two to three hours and thereafter the distorted tape remains in about the same configuration. Hence a reading taken at the beginning of the period cannot be accurately compared with a subsequent reading.

SUMMARY OF THE INVENTION

One of the principal objects of the present invention is to provide an apparatus and process for accurately examining cards in which microorganisms are incubated. Another object is to provide an apparatus and process of the type stated which has the ability to disregard bubbles in wells of the cards and to provide readings which reflect the true optical characteristics of the dehydrated media in the wells. A further object is to provide an apparatus and process which compensates for the distortion of the optical properties of a well due to tape deflection. An additional object is to provide an apparatus and process of the type stated which greatly diminishes the likelihood of foreign particles and stray markings producing a false reading of the indicia marked on a card. These and other objects and advantages will become apparent hereinafter.

The present invention is embodied in a machine including the reading head capable of supporting a card having a viewing well which contains a culture medium which is hydrated by a diluted specimen. A first light emitter is mounted on the reading head to project light through the viewing well, and a plurality of first light detectors are also mounted on the reading head beyond the opposite surface of the card, these detectors being aligned with the light emitter so as to be illuminated by the emitter. The invention is also embodied in a process including projecting light through a viewing well, and detecting the light which passes through the well at a plurality of locations to determine the intensity of the light at each location. The invention also consists in the parts and in the arrangements and combinations of parts hereinafter described and claimed.

DESCRIPTION OF THE DRAWINGS

In the accompanying drawings which form part of the specification and wherein like numerals and letters refer to like parts wherever they occur:

FIG. 1 is a perspective view, partially exploded, showing the machine for reading cards containing medical specimens, a card being illustrated removed from its holder;

FIG. 2 is a plan view of an identification card into which medical specimens are introduced;

FIG. 2A is a plan view of an antibiotic susceptibility card;

FIG. 3 is a sectional view of the identification card taken along line 3—3 of FIG. 2;

DETAILED DESCRIPTION

Figure 4:
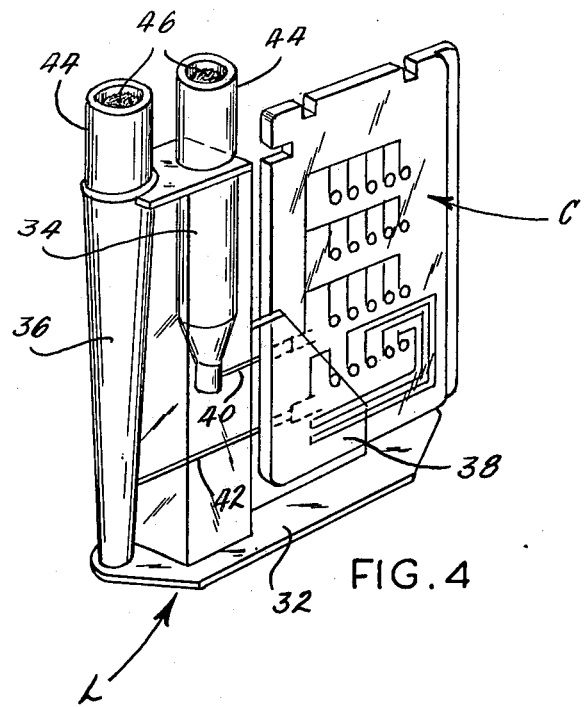
FIG. 4 is a perspective view of the loading device for the card, with a card being inserted into it.

Referring now to the drawings, a microbial analyzing machine A (FIG. 1) examines cuvettes or cards C into which specimens suspected of containing harmful microorganisms have been introduced. The card C contains dried selective media which is rehydrated by the diluted specimen. If the specimen contains a microorganism to which one of the media is selective, then the optical characteristics of that particular rehydrated medium will change as the microorganism metabolizes in the medium during incubation. The machine A detects the changes in light transmitting characteristics of the rehydrated media by projecting light through the rehydrated media. In addition, the reading machine A detects indicia marked on the cards C and is capable of distinguishing the ten basic cardinal numbers written as Arabic symbols. These readings are also accomplished by projecting light through the cards C.

The machine A includes a holder H and an extracting unit E (FIG. 5), and the latter is provided with a card reading unit R which reads the indicia on the cards C and examines the rehydrated media for changes in the light transmitting characteristics thereof. The holder H supports a plurality of cards C in a row with the margins of the cards C being in registration. All the cards C of the row have the same orientation. The extracting unit E withdraws the cards C individually from the row and each card C as it is withdrawn is examined by the reading unit R. Indeed, each rehydrated medium is examined separately and at periodic intervals.

The machine A is controlled by a computer K, and the media and indicia readings derived from the reading unit R are fed to that computer. The computer K correlates the various media and indicia readings so that the periodic readings derived from particular rehydrated medium of a particular card C are organized in succession. This enables one to determine if any change in the light transmitting characteristicsmachine A, one being an identification card $C_i$ (FIG. 2) and the other being an antibiotic susceptibility card $C_s$ (FIG. 2A). The identification card $C_i$ is used to identify microorganisms in the specimen which is introduced into it, while the susceptibility card $C_s$ is used to ascertain the effect of antibiotics on microorganisms identified with the card $C_i$. Both cards $C_i$ and $C_s$ have identical external configurations and hence will for the most part be described merely as the card C.

The major component of the card C is a clear plastic plate 2 (FIGS. 2 and 3) possessing a rectangular configuration. Preferably the plate 2 is 3.59 inches long, 2.24 inches wide, and 0.125 inches thick. Along one of its front margins, the plate 2 has two outwardly opening positioning notches 4, while along each of its side margins it is provided with a gripping slot 6. The slots 6 are located quite close to the front margin out of which the notches 4 open. Along one of the side margins, the plate 2 is provided with a kerf 8 which imparts a stepped configuration to the plate 2 at that side margin. The other side margin has a shallow retaining notch 9 opening out of it, as well as a pair of filling bores 10 which have elastomeric septa 12 fitted tightly into them. Each bore 10 in turn leads into a separate receiving chamber 14, and these chambers open out of the upper of the two major surface areas on the plate 2.

The plate 2 is further provided with a plurality of viewing wells 16 which are circular apertures extending completely through the plate 12. Each well 16 is somewhat conical and possesses a greater cross sectional area at the upper surface of the plate 2 than at the lower surface. The wells 16 are arranged in four rows with the rows extending transversely, that is parallel to the front and rear margins. Each well 16 has a pair of overflow channels 18 radiating from it toward the front margin, and these channels likewise extend completely through the plate 2. The wells 16 of the first three rows are connected to the first receiving chamber 14 by a filler channel 20 which is narrow shallow groove opening out of the upper surface of the plate 2. The channel 20 branches a slight distance beyond the first receiving chamber 14 and thereafter branches again so that a separate branch leads into each well 16. This isolates the wells 16 of the first three rows from each other. The wells 16 of the last row are connected to the second receiving chamber 14 through more filler channels 22 which likewise open out of the upper surface of the plate 2 and are arranged to isolate the several wells 16 of that row from one another.

Adjacent to the kerf 8 the plate 2, on its underside, is provided with an identification segment 24 which is a very shallow identation resembling the Arabic numeral eight in block form. Thus, the segment 24 consists of a parallel top, intermediate, and bottom bars, as well as four side bars connecting the ends of the top, intermediate, and bottom bars. The segment 24 is stippled so as to that ink markings placed on any one of the bars will easily adhere in a uniform manner. The segment 24 provides an outline in which any of the ten basic numbers may be marked. Beyond the segment 24, one or more code segments 26 are applied to the plate 2, these being opaque markings which align with the upper or lower side bars of the segments 24 or the top, intermediate or bottom bars of the segment 24. The code segments 26 are utilized to identify the type of test for which the particular card C is designed. In the case of the identification cards $C_i$ a code segment 26 at one location may indicate that the particular card $C_i$ is for conducting an analysis on urine specimens, while a code segment 26 at another location may indicate that the card $C_i$ is for a throat specimen. Beyond the code segments 26 are a succession of patient identification segments 28 which are arranged in a row parallel to the side edge of the card C. Each segment 28 resembles the block numeral 8. The segments 24, 26 and 28 lie in a row parallel to the kerf 8.

Most of and in some cases all of the viewing wells 16 contain a dehydrated culture media, and these media are selective in the sense that when rehydrated they will change the optical characteristic of the wells 16, but only when sustaining the particular microorganisms to which they are specific. For example, one well 16 may contain a culture medium which is specific to pseudomonas aeruginosa, while another well 16 may contain culture medium which is specific to staphylococcus aureus. The change in optical characteristics is usually the result of increased turbidity or a change in color. Some of the wells 16 may be left empty for purposes of control.

Each major surface area of the plate 2 is covered with a transparent tape 30 which is wide enough and long enough to completely extend over and close the ends of the viewing wells 16 and the ends of the overflow channels 18. The tape on the upper surface area furthermore extends over and closes the receiving chambers 14 and the filler channels 20 and 22. Thus the tapes 30 together with the septa 12 isolate the receiving chambers 14, the wells 16, the overflow channels 18, and the filler channels 20 and 22 from the surrounding atmosphere and prevent the entry of contaminants into the wells 16. The tapes 30 are slightly permeable in that they will admit air to the wells 16, but the permeability is such that neither water nor microorganisms can escape from the wells 16. Furthermore, the tapes 30 admit air so slowly that they permit the interior of the wells 16 to be placed under a vacuum of at least 28 inches Hg and held at that condition for at least 3 minutes. FEP 5430 tape marketed by the 3M Company is suitable for the tapes 30.

The card C is loaded with a diluted specimen in a loading device L (FIG. 4) including a flat base 32, short and long tubes 34 and 36 projecting upwardly from the base 32 parallel to each other, and a pair of parallel guide webs 38 interposed between the base 32 and the short tube 34. The spacing between the webs 38 is slightly greater than the thickness of the card C so that the card C may be fitted between them. The tubes 34 and 36 have hollow needles 40 and 42 projecting radially from their lower ends and into the space between the webs 36. The spacing between the needles 40 and 42 equals the spacing between the bores 10 in the plate 2, while the distance between the lower needle 42 and the base 32 equals the distance between rear end edge on the card C and the rear filling bore 10. Hence, when the card C is inserted between the webs 36 with its rear edge resting on the base 32 and the bores 10 presented toward the tubes 34 and 36, the needles 40 and 42 will align with the septa 12. To couple the card C with the loading device L, the card C is advanced toward the tube 34 until the needles 40 and 42 are projected through the septa 12. This provides communication between the interior of the tubes 34 and 36 and the interior of the card C. The upper end of each tube 34 and 36 is open and is fitted with a removable stack 44 containing a wad of cotton 46 which serves as a filter.

The specimen is diluted in 0.5% saline solution (Na Cl) and the dilution so formed is placed in the short tube 34. A known volume of pure saline solution is placed in the longer tube 36 and thereafter a known quantity of dilution is withdrawn from the short tube 34 by means of a pipette and released into the long tube 36, thus effecting a further dilution. Thereafter the stacks 44 are fitted over the tubes 34 and 36 and the loading device L and card C are placed in a vacuum chamber where the pressure is reduced to about 28 inches Hg. This causes air within the wells 16, the overflow channels 18, the filler channels 20 and 22 and the receiving chambers 14 to pass out of the card C through the needles 40 and 42 and to bubble through the dilutions in the tubes 34 and 36. The vacuum is held for about 3 minutes, whereupon it is released, permitting normal atmospheric pressure to again exist at the upper surface of the dilutions. This forces the dilutions through the needles 40 and 42 and into the receiving chambers 14 of the card C. The dilutions continue through the filler channels 20 and 22 to the wells 16 where they mix with and rehydrate the selective culture media in the wells 16. Any entrapped air migrates to the overflow channels 18, which are directed upward when the card C is loaded.

The susceptibility cards $C_s$ are quite similar to the identification cards $C_i$, except for the fact that they have fewer wells 16 and the filler channels are arranged somewhat differently. Furthermore, all filler channels lead to a single receiving chamber 14 and septa 12, so that the cards $C_s$ are filled with a loading device having only one tube 34 and one needle 40. While the card $C_s$ has fewer wells 16 than the cards $C_i$, the wells 16 which do exist occupy positions which are exactly the same as the wells 16 the card $C_i$. In other words, if the susceptibility card $C_s$ is placed over the identification card $C_i$, the wells 16 in both would be in registration. Also the selective media in the wells 16 of the susceptibility card $C_s$ contains antibiotics. Of course, the code segments 26 of the card $C_s$ are arranged differently to indicate not only that the card $C_s$ is for antibiotic susceptibility tests, but also to indicate the type of microorganism for which the susceptibility test is designed. The susceptibility card $C_s$ is described in more detail in U.S. Pat. No. 3,957,583.

Selective culture media suitable for use in the identification cards $C_i$, are disclosed in U.S. Pat. No. 3,963,355 as well as in patent applications filed contemporaneously herewith and assigned to the McDonnell Douglas Corporation. The same culture media when mixed with various antibiotics are suitable for use in the susceptibility cards $C_s$.

The Holder

The holder H supports the cards C in a stack with the major surface areas of the cards C being parallel and spaced apart and with the positioning notches 4 and the gripping slots 6 presented outwardly. The stack of cards C is located opposite the extracting unit E.

The holder unit H includes a rotatable carrousel 48 (FIG. 5) and trays 50 on the carrousel 48. The trays 50 hold the cards C, while the carrousel 48 holds the trays 50 and rotates them to a reading position opposite the extracting unit E. Each tray 50 (FIGS. 1, 5 and 11) has a front flange 52 which surrounds a cavity 54. The back of the cavity 54 is open to enable heated air to be circulated through the cavity 54. Projecting into the cavity 54 from its sides are fins 56 (FIG. 11) which define a plurality of card receiving slots 58. These slots 58 are sized to receive the cards C, and when the cards C are within the slots 58 their major surface areas are parallel. Also, the major surface areas of adjacent cards C are spaced apart slightly.

Along the left side of each slot 58 is a key 60 (FIG. 5) which is configured to fit into the kerf 8 of the card C inserted into that slot 58. The key 60 permits the card D to be inserted into the slot 58 in only one orientation, that being with the identification segments 24, 26 and 28 facing downwardly and the positioning notches 4 and gripping slots 6 presented outwardly beyond the front flange 52. At the side of each slot 58 is a resilient retaining finger 62 having a nib at its end, and this nib fits into the retaining notch 9 for the card C in that slot 58 when the card C is fully inserted.

The holder H is further provided with a heater and fan unit 64 which directs heated air into the carrousel 48 from which it is discharged into the rear of the cavities 54 in the trays 50. This air flows through the spaces between the cards C, and in so doing passes along the major surface areas of the cards C. The heated air maintains the cards C at a temperature suitable for incubating any cultures which may establish therein.

The Extracting Unit

The extracting unit E withdraws the cards C individually from that tray 50 which is in the reading position and then reinserts them so that the wells 16 and the identification segments 24, 26, and 28 may be viewed by the reading assembly R. The identification segments 24, 26, and 28 are observed as the cards C are withdrawn, while the wells 16 are examined as the cards C are reinserted.

The extracting unit E includes a main frame 68 (FIG. 5) which is stationary and a reading head 70 which moves upwardly and downwardly on the frame 70 parallel to the stack of cards C in that tray 50 of the holder H which is in the reading position. This movement is derived from a direct current stepping motor 72 which rotates a vertical drive screw 74, that screw threading through a nut 76 on the head 70.

Figure 9:
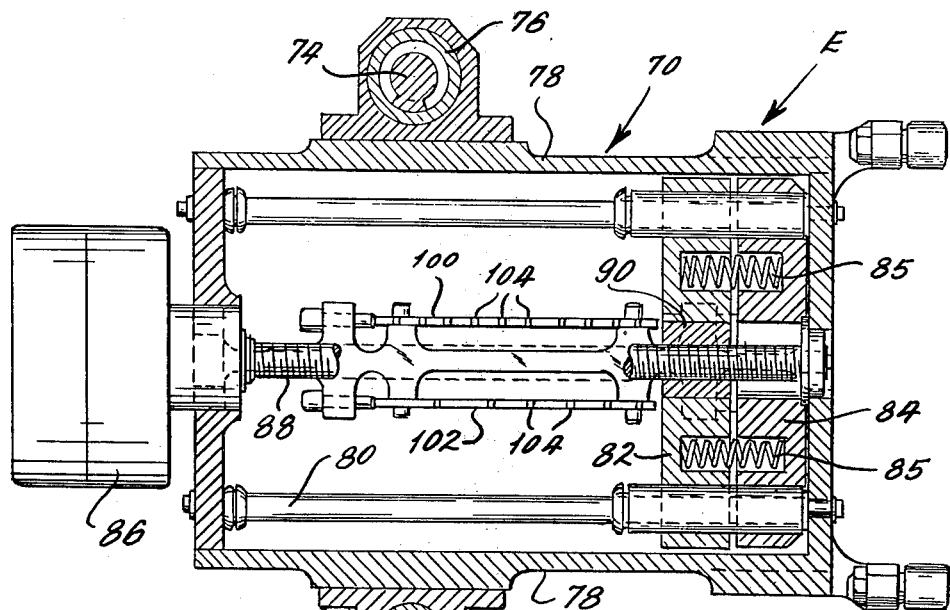
FIG. 9 is a sectional view of the reading head taken along line 9—9 of FIG. 7.

The head 70 (FIG. 6) includes a main body or block 78 having horizontal slide rods 80 (FIG. 9) on it. These rods 80 extend parallel to the slots 58 in the holder H and support an extractor slide 82 (FIGS. 7, 9 and 10) and a locator slide 84, both of which move in the direction of the rods 80. The locator slide 84 is furthermore capable of moving relative to the extractor slide 84 with the direction of relative movement also being parallel to the rods 80. Interposed between the two slides 82 and 84 are coil-type compression springs 85 (FIG. 9) which urge the slides 82 and 84 apart, but the locator slide 84 has stops which limit the distance which that slide may move away from the extractor slide 82. The slides 82 and 82 are moved along the rods 80 by another direct current stepping motor 86 which rotates a horizontal drive screw 88 located between the two rods 80, and this screw threads through a nut 90 in the extractor slide 82.

Figure 10:
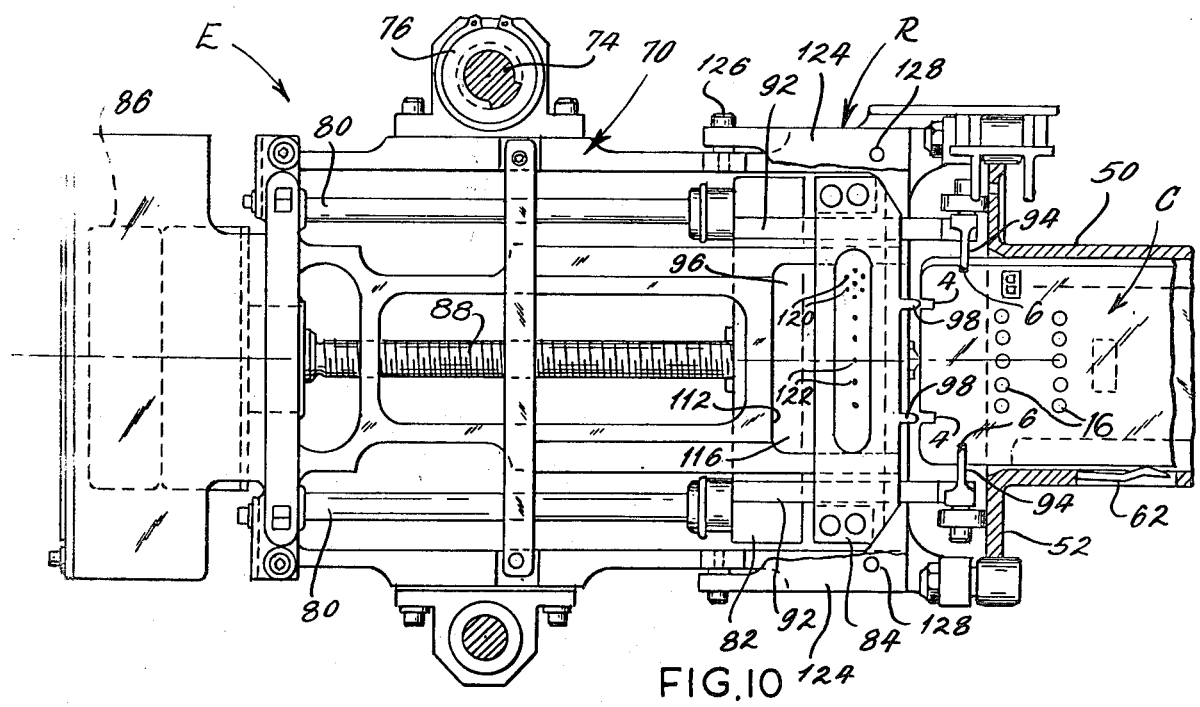
FIG. 10 is a plan view of the reading head in position to extract a card from the holder.

The extractor slide 82 has two arms 92 (FIGS. 7 and 10) which project upwardly and forwardly, and these arms at their ends are fitted with gripping claws 94. The size of and the spacing between the gripping claws 94 is such that the claws 94 when lowered from above the cards C, will fit into the gripping slots 6 of the cards C (FIG. 10). The locator slide 84 has a positioning plate 96 bolted to it, and this plate is located over the top surface of the main block 78 on the reading head 70. The positioning plate 96 has two forwardly projecting positioning prongs 98 which are at the same elevation as the gripping claws 94 and align with the positioning notches 4 in the cards C. The springs 85 are positioned such that they urge the positioning prongs 98 toward the gripping claws 94. However, when the extractor slide 82 is in its forwardmost position, that is the position at which its gripping claws 94 are at the gripping slots 6 in the cards C (FIGS. 7, 9, and 10), the locator slide 84 will be against a limiting surface on the main block 78. When the slide 84 is so disposed, the positioning prongs 98 of its plate 94 are incapable of projecting fully into the positioning notches 4 on the cards C (FIG. 10). In other words, the prongs 98 are backed off slightly from the notches 4.

Once the head 70 is lowered with the vertical motor 72 to bring the gripping claws 94 into gripping slots 6 of a card C, and the horizontal motor 86 is thereafter energized to retract the extractor slide 82, the claws 94 will pull the card C outwardly and bring notches 4 into engagement with the prongs 98 of the locator slide 84. At this point the prongs 98 will bottom out against the bases of the notches 4, and the locator slide 84 will be driven rearwardly by the extractor slide 82, with the driving force being transmitted through the card C. The locator slide 84 thus moves in unison with the extractor slide 82 (FIG. 11) and in so doing maintains a constant force on the front of the card C, that force being exerted by the springs 85. The spring force maintains the card C in a predetermined orientation with respect to the reading head 70.

Figure 8:
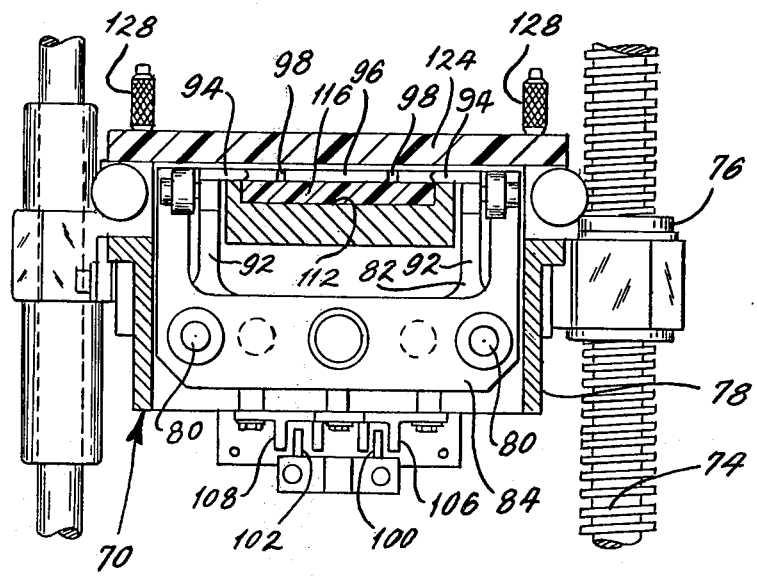
FIG. 8 is a sectional view of the reading head taken along line 8—8 of FIG. 7.

The main block 78 of the reading head 70 has two control bars 100 and 102 (FIGS. 8 and 9) attached to it below the slides 82 and 84, and these bars have notches 104 (FIGS. 6 and 7) therein along their upper margins. The spacing between successive notches 104 of the bar 100 equals the spacing between successive identification segments 24, 26, and 28 on the card C, while the spacing between the notches 104 of the bar 100 equals the spacing between the rows of viewing wells 16 in the card C. The control bar 100 is monitored by a bifurcated optical switch 106 (FIGS. 7 and 8) which is on the locator slide 84 and controls the motor 86 as it moves the extractor slide 82 away from the holder H, that is when it extracts the card C. One tine of the bifurcated switch 106 carries a light emitting diode which is directed toward one side of the bar 100, while the other tine is located on the opposite side of the bar 100 and carries a phototransistor which is directed toward the light emitting diode. Normally, diode and transistor face the opaque portion of the bar 100, but when the switch 106 moves, one of the notches 104 will come between the diode and transistor, at which time the diode will illuminate the transistor and a signal will be generated. This signal is directed to the computer K which stops the horizontal motor 86 momentarily. The control bar 102 is monitored in an identical manner by another optical switch 108 (FIGS. 6 and 8) which is also mounted on the locator slide 84, and that switch controls the motor 86 as the motor 86 moves the extractor slide 82 back toward the holder H. Thus, each time the switch comes to a notch 104 in the bar 102, it sends a signal to the computer K which stops the motor 86 for a short duration.

The extractor slide 82 carries a stop tab 110 (FIG. 6) which is normally located beyond the switch 108. However, as the card C approaches its fully inserted position, the locator slide 84 and the switch 108 upon it will come to rest, while the extractor slide 82 continues to move. Indeed, the extractor slide 82 continues to advance until the stop tab 110 moves between the diode and phototransistor of the switch 108 and interrupts the beam of light, at which time a signal is sent to the computer K which in response stops the motor 86 and the extractor slide 82 driven by it.

Figure 11:
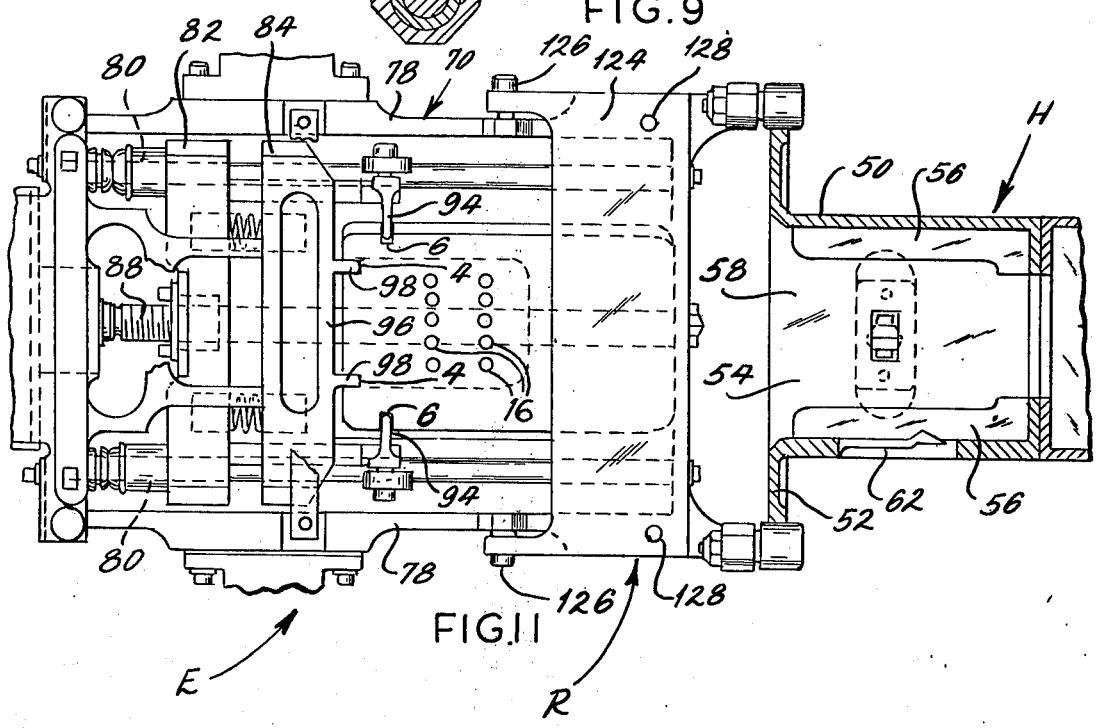
FIG. 11 is a plan view of the reading head with the card completely extracted from the holder.

The top surface of the main block 78 is for the most part flat, and the card C, as it is withdrawn from the holder H and thereafter reinserted into it, passes directly over this flat surface (FIG. 11). The block 78 contains a recess 112 (FIG. 10) which opens out of the flat surface adjacent to the forward end wall of the block 78.

The Reading Unit

The reading unit R is carried by the reading head 70 (FIGS. 7 and 10) and examines a different identification segment 24, 26, and 28 with each momentary hesitation of the card C as it is withdrawn from the holder H. In this regard, the control bar 100 and switch 106 control the withdrawal of card C, and each time the switch 106 encounters a notch 104 in the bar 100, a momentary hesitation in the withdrawal occurs. The reading unit R likewise examines the viewing wells 16, this occurring with each momentary hesitation during the reinsertion of the card C into the holder H. These momentary hesitations occur each time the optical switch 108 encounters a notch 104 in the control bar 102, and this enables the examination of the wells 16 to proceed on a row-by-row basis.

Figure 12:
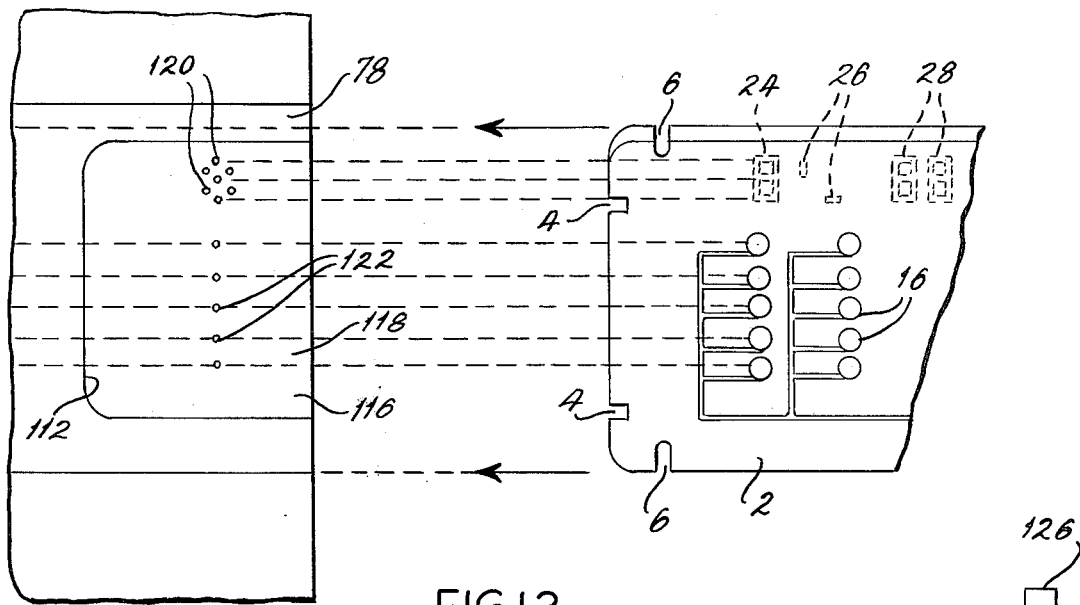
FIG. 12 is a view of the reading unit taken along line 12—12 of FIG. 6 and showing identification segments and viewing wells of a card aligned respectively with the digit emitters and well emitters of the reading unit.
Figure 14:
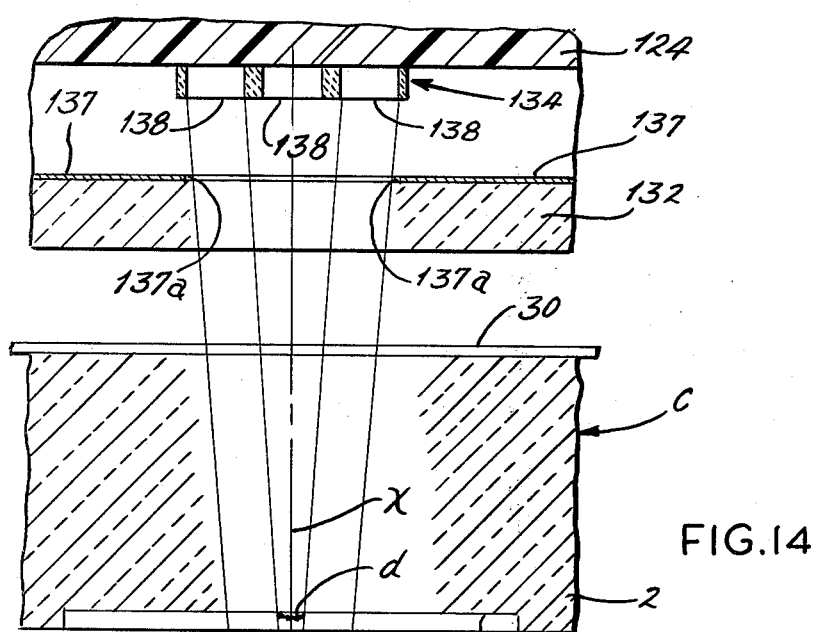
FIG. 14 is a sectional view of one of the digit emitters and digit sensors with a card being interposed between the two such that the light from the emitter projects through an identification segment on the card.
Figure 15:
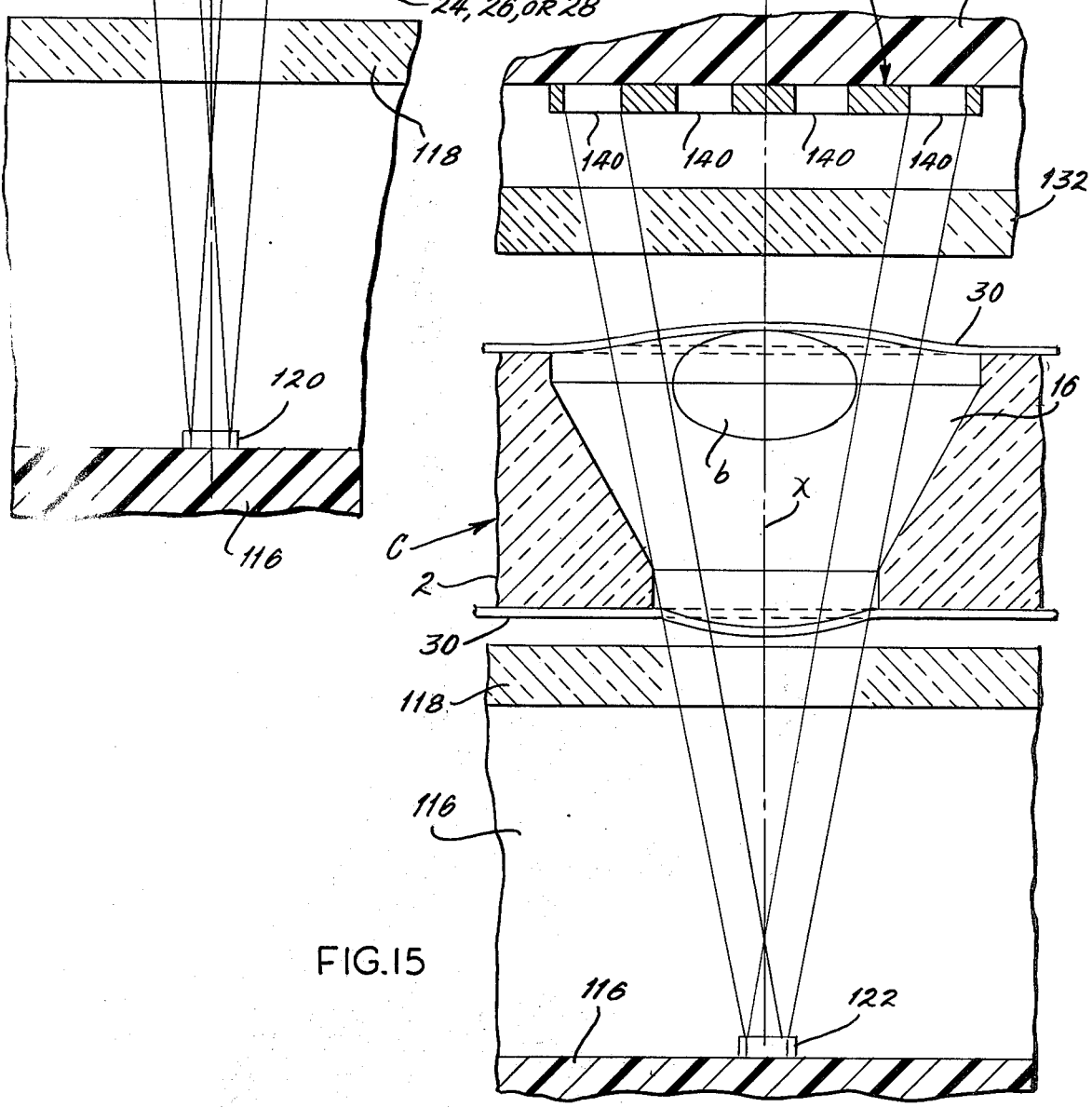
FIG. 15 is a sectional view of the reading unit at one of the well emitters and its corresponding well sensor, with a card being interposed between the two such that the light from the emitter passes through a viewing well on the cards.

The reading unit R includes a dielectric plate 116 (FIGS. 10 and 12) which fits into the recess 112 of the main block 78 on the reading head 70, along with a protective cover glass 118 (FIGS. 14 and 15). The upper surface of the glass 118 lies slightly below the flat top surface of the block 78. The plate 116 contains seven digit emitters 120 (FIG. 12) which are light emitting diodes oriented to direct the light emitted thereby upwardly. The array so formed is positioned such that the identification segments 24, 26, and 28 on the card C will pass over it as the card C moves over the block 78. Indeed, at each momentary hesitation of the card C during its withdrawal, a different identification segment 24, 26, or 28 will be located directly over the array of digit emitters 120. Thus, the digit emitters 120 occupy a relatively small area located at one side of the dielectric plate 118. The seven digit emitters 120 are arranged in the pattern of an Arabic numeral eight, with each emitter 120 occupying a different bar of the numeral. Moreover, the positioning is such that when any one of the identification segments 24 or 28 is directly above the array of emitters 120, that is, in the position in which the momentary hesitation in the withdrawal occurs, each bar of the segment 24 or 28 will be located above a different emitter 120. Any bar of that segment which has an opaque ink marking on it will of course block out the emitter 120 below it so that only the emitters 120 at the unmarked bars are visible above card C. The code segments 26 align with the top, middle, or bottom emitters 120 of the figure eight array, or the four emitters 120 located along the side of the figure eight array.

Thus, when the card C comes to rest at the first code segment 26, only that emitter 120 which is located below the segment 26 will obscured. The same is true as the card C stops with subsequent code segments 26 over the array of emitters 120.

In addition to the digit emitters 120, the dielectric plate 116 contains five well emitters 122 (FIG. 12) which are arranged in a row across the plate 116 and are likewise oriented such that the light emitted thereby is projected upwardly. The row extends transversely of the direction in which the card C is moved over the plate 116 and the spacing between the well emitters 122 is equal that the spacing between the individual viewing wells 16 of a row of wells 16 in the card C. Moreover, the location of the emitters 122 in relation to the notches 104 in the control bar 102 is such that the bar 102 causes a momentary hesitation in the card C each time a row of viewing wells 16 is directly over the row of well emitters 122. When this occurs, the well emitters 122 project light through the viewing wells 16 of the row, and the amount of light which passes is in most instances a measure of the metabolic activity within the wells 16. The emitters 120 and 122 should emit light having a wave length of 660 nanometers.

The reading unit R also includes another dielectric plate 124 (FIGS. 6, 8, and 11) which overlies the recess 112 with the spacing between the flat top surface of the block 78 and the underside of the plate 124 being slightly greater than the thickness of the cards C, thus enabling a card C which is withdrawn from the holder H to pass between the two dielectric plates 116 and 124. The dielectric plate 124 is hinged to the main block 78 at hinge pins 126 which are located to the rear of the recess 112 so that the plate 124 may be swung upwardly to expose the recess 122 and the plate 116 within it. When the plate 124 is in its lower or operating position, locating pins 128 fit through it and into the block 78 to precisely position the plate 124 over the plate 116. The plate 124 is secured in its lower position by overcenter clamps 130 (FIG. 6) which are attached to the sides of the main block 78.

The upper dielectric plate 124 contains a cover glass 132 (FIGS. 14 and 15) which is presented downwardly directly opposite from the cover glass 118 for the lower dielectric plate 116, with the spacing between the two cover glasses 118 and 132 being slightly greater than the thickness of the cards C so that a card C will pass between them. The dielectric plate 124 is fitted with seven digit sensors 134 (FIG. 13) and five well sensors 136 which are capable of detecting light, and these sensors are connected with the computer K and provide signals which correspond to the amount of light falling upon them. The digit sensors 134 are located opposite the digit emitters 120 with each digit sensor 134 being located opposite and illuminated by a different digit emitter 120. Hence, the digit sensors 134 are also arranged in the pattern of the Arabic numeral eight. The well sensors 136 are alinged with the well emitters 122 with each sensor 136 being located opposite to and illuminated by a different emitter 122. Hence the well sensors 136 are arranged in a row extended transversely of the direction in which the card C is moved over the block 78. That portion of the cover glass 132 which is in front of the digit sensors 134 is provided with an opaque reflective coating 137 (FIG. 14), but this coating has windows 137a so that transparent areas exist opposite the sensors 134. A separate window 137a exists opposite each sensor 134 with the window 137a being about the same size and configuration as the sensor 134 behind it. The reflective coating 137 and its windows 137a confine the light of each digit emitter 120 to its corresponding digit sensor 134. Thus, light from one digit emitter 120 will not illuminate the sensors 134 for the adjacent emitters 120, even though the sensors 134 are located very close together.

Figure 13:
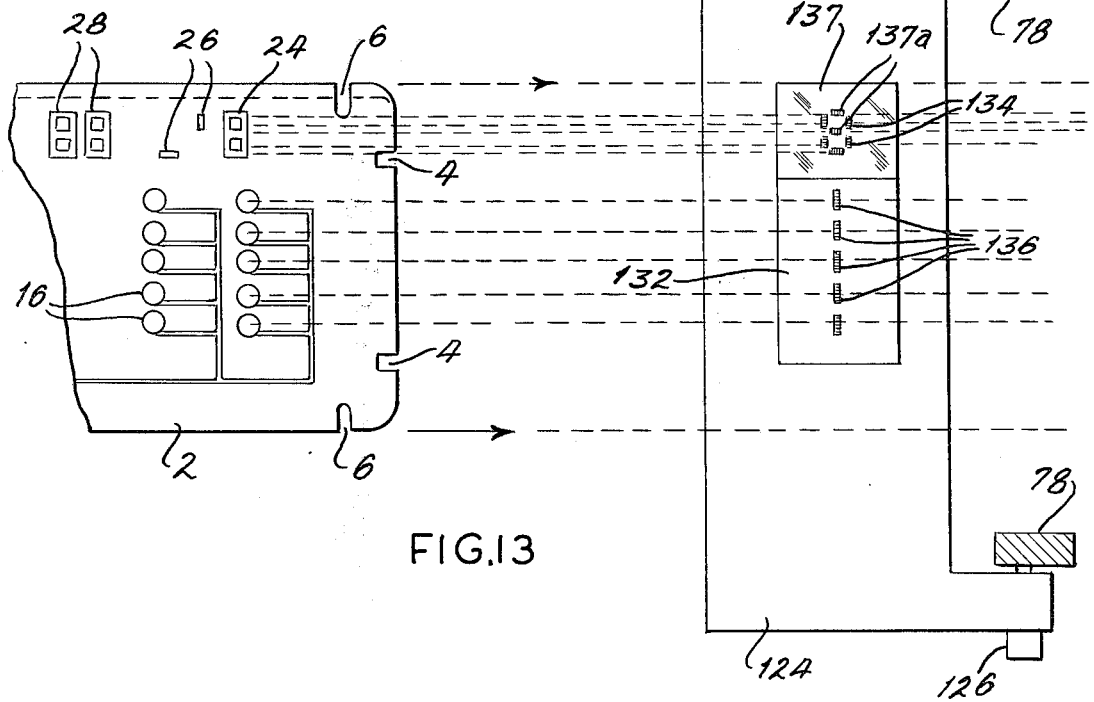
FIG. 13 is a view of the reading unit taken along line 13—13 of FIG. 6 and showing the identification segments and viewing wells of a card aligned respectively with the digit sensors and well sensors of the reading unit.

Each digit sensor 134 comprises a plurality of light detectors 138 (FIG. 14) which are arranged in a row so that some of the detectors 138 are offset from the optical axis $x$ of the beam projected by the corresponding emitter 120. Moreover, the orientation of each row corresponds to the orientation of the bars on the identification segments 24, 26, or 28 which will pass under them (FIG. 13). For example, the rows of detectors 138 for the digit sensors 136 which overlie the top, middle, and bottom bars of the identification segments 24 and 28 extend parallel to the direction in which the card C is moved over the block 78, while the rows of detectors for the digit sensors 138 which overlie the side bars of the identification segments 24 and 28 extend perpendicular to the direction of movement for the card C. Thus, the array of digit sensors 134 forms an Arabic numeral eight in block form. Each digit sensor 134 preferably consists of a row of three detectors 138 (FIG. 14), and each detector 138 may be a separate phototransistor, that is a transistor which is sensitive to light and provides a signal which is proportional to the intensity of the light falling upon it. The arrangement of the detectors 138 is such that the detectors 138 of any sensor 134 are illuminated only by the emitter 120 corresponding to that sensor 134, and only then when not obscured or blocked out by a bar on one of the identification segments 24, 26, or 28 of the card C. For example, if the numeral 3 is written in the identification segment 24 of the card C in opaque ink, the detectors 138 of the top, middle, and bottom digit sensors 134 and the detectors 138 of two sensors 134 along one side of the array will be obscured from their corresponding emitters 120 when the card C is positioned with the identification segment 24 between the array of digit emitters 120 and digit sensors 134. The opaque reflective coating 137a on the cover glass 132 prevents light from one emitter from falling upon the sensors 134 which align with other emitters 120.

Each detector 138 of the seven digit sensors 134 provides the computer K with a separate reading. The computer K is programmed such that two out of the three detectors must cross a prescribed threshold value before the particular bar of the identification segment 24, 26, or 28 which is being examined is considered to be transparent, that is free of opaque markings. Thus, a speck of dirt $d$ or a stray marking in one of the bars of the identification segment 24, 26, or 28 may block out one of the detectors 138 of the sensor 134 for that bar, but not the other two and the other two will provide a signal which crosses the threshold value, indicating that this particular bar is unmarked. This is in contrast to a single detector 138 illuminated by a single emitter 120 where a speck of dirt or stray marking could lower the overall signal derived from the detector to below the threshold value and thus provide a false reading. The use of multiple detectors 138 for each digit emitter 120 is called the voting technique.

The voting technique is also used in conjunction with corresponding well emitters 122 and well sensors 136, for each sensor 136 consists of a plurality of detectors 140 (FIG. 15) focused on the emitter 122 for that sensor 136. Preferably four detectors 140 are used in each sensor 136, and these detectors are arranged in rows along a common axis extended transversely of the direction of movement for the cards C under the plate 124. Hence all of the detectors 140 for a sensor are offset from the optical axis $x$ of the light beam projected by the corresponding emitter 122. The individual detectors 140 of the well sensors 136 are connected to the computer K and when illuminated provide the computer K with signals which are proportional to the light falling upon them. That light is, of course, emitted by the well emitters 122, and its intensity is decreased upon passing through a viewing well 16 in the card C.

As to the detectors 140 of the well sensors 136, the computer K looks for the percentage reduction in light transmission from an initial calibration value. A threshold value is established, beyond which a selected number and for example all four detectors 140 must cross before the well 16 is considered to contain the microorganism to which the culture medium for that well 16 is specific. Before this threshold value is reached, the reading derived from the detector 140 providing the lowest reduction in light transmission is recorded and considered the reading for the well 16 at that particular time.

The foregoing voting technique enables the reading unit R to provide meaningful observation of a well 16 even though bubbles $b$ (FIG. 15) may form in that well. In this regard, it is not uncommon for bubbles to develop in at least some of the wells 16 since from a practical standpoint it is impossible to evacuate all of the air from the cards C during the vacuum loading. While most of the entrapped air remains in the overflow channels 18, some may migrate into a viewing well 16, creating an air bubble $b$ therein. Furthermore, some of the microorganisms produce gases as they metabolize, thus providing another source of bubble formation. The bubbles $b$ appear opaque and consequently cause the detectors 140 which are obscured by them to register a very high reduction in light transmission. However, the bubbles do not occupy the entire width of the wells 16 in which they locate. Hence it is necessary to look around them and this is precisely what the voting technique accomplishes.

An examination of the foregoing nature is conducted on each viewing well 16 at periodic intervals which should not be in excess of about one hour. Usually about three hours are required before any change in the light transmitting characteristics of a well 16 occurs, assuming that the specimen introduced into it contains the microorganism to which the culture medium of the well 16 is specific. Therefore, it would seem that the reading derived from the detectors 140 of the well sensor 136 which monitors that well 16 would show a substantially constant light transmission, with the reduction in light transmission from the calibration value being below the threshold value. In many instances this is not the case, due to so-called lensing.

Figure 16:
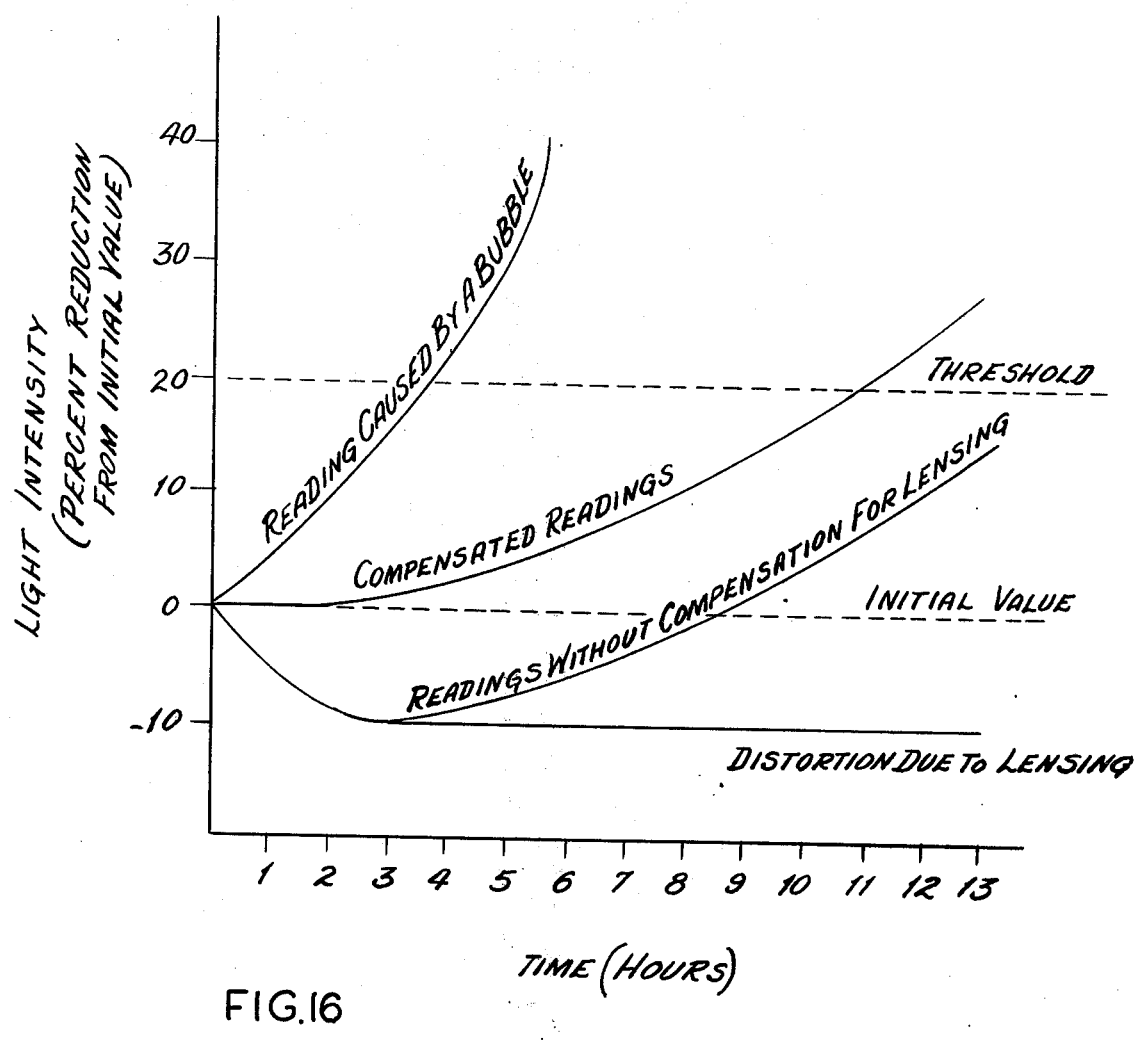
FIG. 16 is a graph showing a typical compensated reading derived from the machine and also the distortion caused by lensing and bubble formation.

Lensing is the distortion error caused by the tendency of the tapes 30 to bulge outwardly into a convex configuration at the ends of the wells 16 (FIG. 15). This is principally the result of liquid or gas expansion caused within the card by the elevation in temperature during incubation. The convex distortion at a well 16 tends to focus more of the light from the emitter 122 for that well 16 on the detectors 140 of the corresponding well sensor 136 than would otherwise be the case. Lensing tends to establish itself during the first two to three hours which is normally before the microorganisms have any major effect on the medium, and thereafter the lensing error remains substantially constant (FIG. 16). Thus, for the first few readings, the detectors 140 may register an increase in light transmission. Once the microorganisms begin to have an effect on the rehydrated medium, a reduction in light transmission begins to occur and progresses with that reduction commencing at the increased value resulting from the lensing.

The computer K registers the increase in light transmission which occurs in initial readings and adjusts all subsequent readings to compensate for this increase (FIG. 16), that is it adjusts the subsequent readings so that they reflect the true change from the initial value and not the change from the distorted value. For example, if a well detector 140 is initially recorded at zero and the first three readings show an increase of 5%, 10%, and 10% respectively, from the initial reading, then it is apparent that the distortion caused by the lensing is 10%. Assuming that the fourth reading is 4% increase from the initial value, this means that microorganisms apparently exist and have caused a 6% reduction in light transmission (10% − 4%) by the fourth hour. If the fifth reading is 9% reduction from the initial value, this means that the true reduction is 19% (10% + 9%). The computer K makes the adjustments automatically and only the true decrease of the light transmission is registered and recorded.

For each viewing well 16 which is read, the computer K must have the following information in its memory bank.

1. The location of the viewing well on the card.
2. The patient number of the card.
3. The initial value for the detectors 140 when used for the card.
4. The threshold value for the well 16 in the particular card.
5. The error caused by lensing.
6. The time of the particular examination.

OPERATION

The dilution of the specimen to be considered is vacuum loaded into the appropriate card C by means of the loading device L (FIG. 4), and during the loading procedure the dilution flows through the receiving chambers 14, and the filler channels 20 and 22, to the viewing wells 16 where it mixes with and rehydrates the culture media in those wells. Any entrapped air accumulates in the overflow channels 18 which are presented upwardly during the loading operation. At the time the card C is loaded, the patient identification number is placed on the card C by marking the appropriate bars of the segments 28 with a marker capable of applying an opaque ink. This marking is on the bottom of the card C and is legible when the card C is turned over. The numbers appear in block form, owing to the configuration of the segments 28. The single identification segment 24 may be marked in a similar manner to distinguish several cards C of the same patient. The code segments 26 are already on the card C, having been applied at the time the cards C were loaded. The segments 26 indicate the type of test for which the particular card C is designed.

Figure 5:
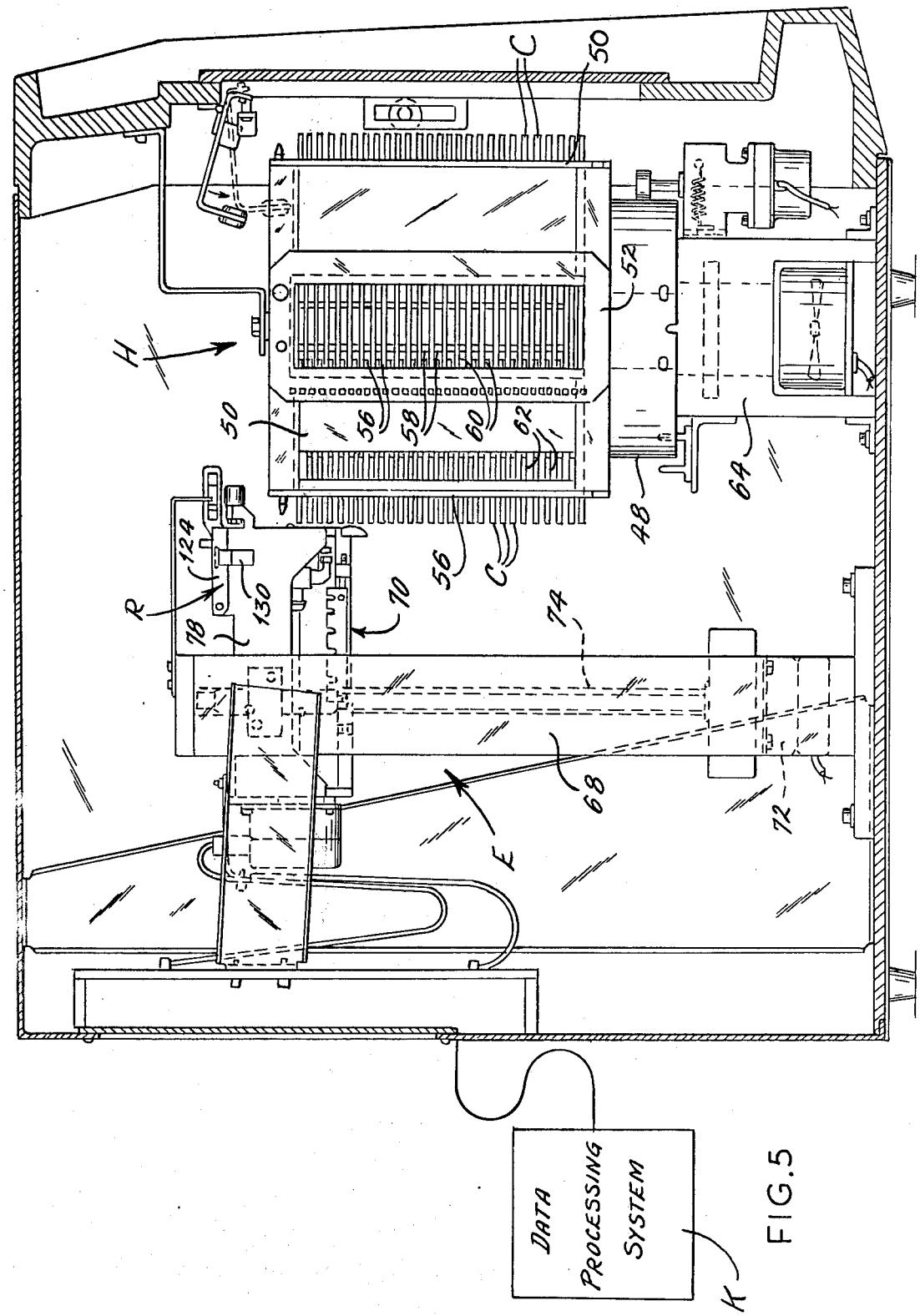
FIG. 5 is a sectional view taken along 5—5 of FIG. 1 and showing the extracting unit and holder in side elevation.

Once the card C is loaded and marked, it is placed in a tray 50 of the holder H by inserting it into one of the slots 58 therein (FIG. 1). The key 60 along the left side of the slot 58 permits the card C to be loaded in only one orientation, that being with the identification segments 24, 26, and 28 facing downwardly and the positioning notches 4 and gripping slots 6 presented beyond the front flange 52 of the holder H (FIG. 5). Many cards C may be loaded into the holder H at the same time and all of these cards C are incubated as a result of the heated air which is passed over their major surface areas (FIG. 5). The cards C within the holder H are arranged in marginal registration, with the stack so formed being presented toward extracting unit E.

The extracting unit E moves downwardly with its extractor slide 82 retracted and the movement continues until the gripping claws 94 on that slide are located just above the first card C. Thereupon, the extractor slide 82 and locator slide 84 move toward the holder H. In time the locator slide 84 comes against the stop surface on the main block 78, and when this occurs the positioning prongs 98 are located close to the notches 4 in the frist card C. The extractor slide 82, however, continues until the stop tab 110 moves into the optical switch 108, interrupting the light emitted thereby (FIG. 6), and when this occurs the extractor slide 82 stops, its gripping claws 94 being directly above the gripping slots 6. The reading head 70 is then lowered sufficiently to bring the gripping claws 94 into the gripping slots 6 and the positioning prongs 98 into horizontal alignment with the positioning notches 4 (FIG. 10). Next the extractor slide 82 is retracted and it withdraws the card C from the holder H (FIG. 11). During the initial increment of movement, the front end of the card C moves toward the positioning prongs 98 and they enter the positioning notches 4 on the card C. When this occurs, the locator slide 84 moves with the extractor slide 82 and exerts a force on the front of the card C. This force is derived from the compressed coil springs 85 and serves to precisely orient the card C in the correct angular and lateral disposition as the card C passes over the block 78.

The extractor slide 82 is propelled by the horizontal stepping motor 86 which continues to operate until the optical switch 106 on the locator slide 84 encounters the first notch 104 in the control bar 100. Here the motor 86 stops momentarily, and at this hesitation a clear portion of the plastic material for the card C is located between digit emitters 120 and the digit sensors 134. The detectors 138 of each digit sensor 134 are calibrated at this point and within the computer K a threshold value is established, beyond which a reading derived from a detector 138 must pass to indicate transparency, that is the absence of a marking between the detector 138 of a digit sensor 134 and the corresponding emitter 120.

After calibration the motor 86 moves the extractor slide 82 until the optical switch 106 encounters the next notch 104 in the bar 100. This places the identification segment 24 between the digit emitters 120 and digit sensors 134. Again a momentary hesitation occurs and at this hesitation the identification segment 24 is read. In particular, the emitters 120 are directed toward the seven bars of the segments 24. If any bar is unmarked, the light from the emitter 120 directly below that bar will pass completely through the bar and illuminate the three detectors 138 of the corresponding digit sensor 134, causing the detectors 138 to provide a signal which exceeds the threshold value (FIG. 14). Since the voting technique is used, a speck of dirt d or stray marking on one of the bars of the segment 24 will not cause a false reading. On the other hand, any of the bars which are purposely blanked out as the result of a number being marked in the segment 24 with opaque ink, will obscure the sensors 134 located opposite to them from their corresponding emitters 120. The detectors 138 of these sensors 134 do not provide a signal which passes threshold value and accordingly the computer K is able to discern the numeral appearing on the identification segment 24.

The identification segments 26 and 28 are read in a like manner, there being a slight hesitation when each successive segment 26 and 28 comes between the digit emitter 120 and sensors 134. The readings derived provide the computer K with the patient identification number and the type of card which is being examined. After the last identification segment 28 reaches the emitters 120 and sensors 134 (FIG. 11), the motor 86 is reversed, and the control of it is transferred to the control bar 102 and its optical switch 108. The extractor slide 82 accordingly moves in the opposite direction and begins to reinsert the card C into the slot 58 from which it was withdrawn.

During reinsertion the motor 86 again makes momentary stops, those stops occurring each time the optical switch 108 encounters a notch 104 in the control bar 102. The first notch 104 in the bar 102 causes the card C to stop with the first row of viewing wells 16 in registration with well emitters 122 and well sensors 136. Here a reading is taken to determine any decrease in light transmitting characteristics of the wells 16 in the first row. Air bubbles $b$ in the wells 16 will appear opaque and obscure the well detectors 140 behind it, but since a bubble will not occupy the whole cross sectional area of the well 16 in which it exists, some of the detectors 140 for the sensor 136 which observes that well 16 will be illuminated by the corresponding well emitter 122 (FIG. 15). The computer K recognizes that a detector 140 showing an extremely high percentage of light reduction is located behind a bubble $b$, and disregards the reading derived from that detector 140. Instead it records only the reading derived from the detector 140 which registers the lowest percentage of light reduction.

Figure 6:
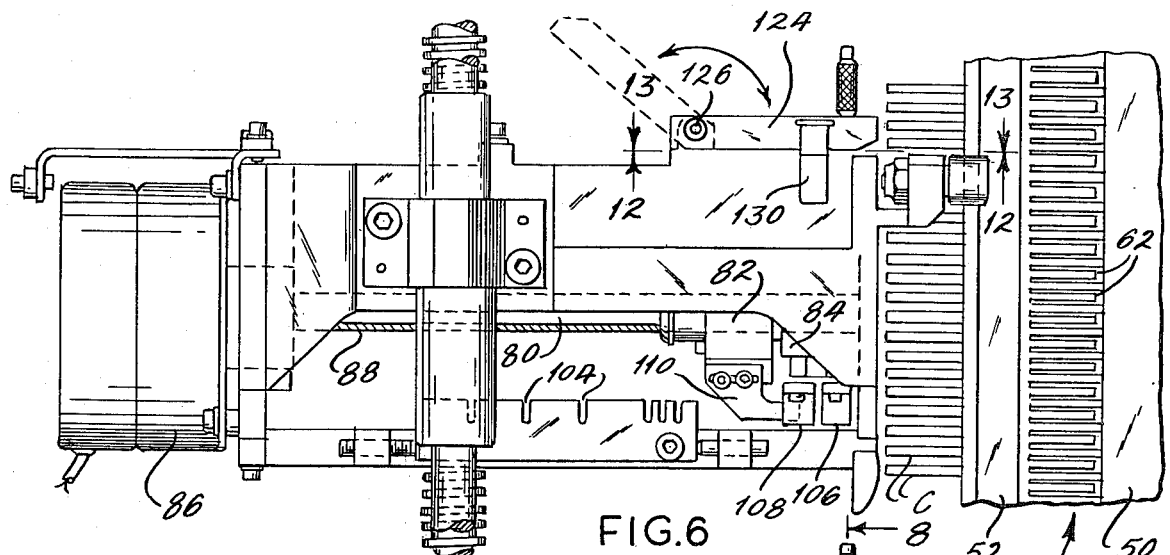
FIG. 6 is a side elevational view of the reading head forming part of the extracting unit.
Figure 7:
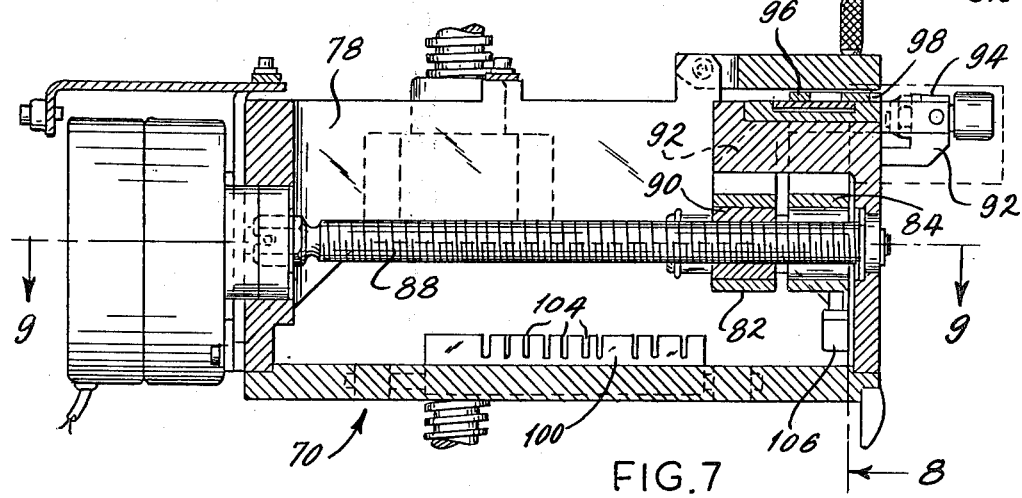
FIG. 7 is a longitudinal sectional view of the reading head.

The motor 86 continues to drive the extractor slide 82 forwardly, with a momentary stop each time a row of viewing wells 16 comes between the well emitters 122 and well sensors 136. Readings are derived at each momentary stop. After the final stop, the motor 86 moves the card C all the way to its fully inserted position within the holder H (FIG. 10). During the last increment of movement the locator slide 84 comes to rest against the stop surface on the main block 78, but the extractor slide 82 continues to move until the stop tab 110 on it moves into the optical switch 108 on the locator slide 84 and interrupts the beam of light (FIG. 6). This completes the handling and reading of the first card C.

Once the first card C is returned to its fully inserted position in the holder H, the reading head 70 drops downwardly and engages the second card C which is withdrawn and read in a like manner. The same procedure occurs for each card C in the holder H. After a predetermined interval, which may be one hour, the entire stack of cards C is again read in a like manner. The procedure is repeated at periodic intervals, of perhaps an hour each, until about 13 hours have elapsed from the initial reading. This provides a set of readings for each well 16 and these readings are organized, compared, and analyzed within the computer K to determine if any well contains the microorganism that well is designed to detect. In other words, if the specimen contains microorganisms to which the culture medium in a well 16 is specific, the well 16 in which that culture medium exists will exhibit a marked decrease in its light transmitting characteristics (FIG. 16).

The microorganisms have little if any effect on the media during the first 2 or 3 hours, and the readings taken during this period are primarily for the purpose of detecting any lensing, and determining the magnitude of it (FIG. 16). Lensing, which always registers as an increase in light transmission due to the tapes 30 assuming a convex configuration at the end of the wells 16, remains substantially constant after about the first 2 hours. The computer K adjusts all subsequent readings to compensate for lensing. These subsequent readings are for the purpose of determing whether or not the microorganism which a specific well 16 is designed to detect is present in that well 16. All detectors 140 observing the well 16 must cross a certain threshold value before the microorganism is considered present. That threshold value represents the minimum decrease in the percentage of light transmission which will be accepted before a well 16 is declared positive and that value is in the computer data bank.

Usually the antibiotic susceptibility cards C are analyzed after the presence of a microorganism is determined as the result of an analysis of an identification card $C_i$. In the case of a susceptibility card $C_s$, the wells 16 which show no or low decrease in the percentage of light transmission over the span of the analysis contain antibiotics which are effective against the microorganism detected with the identification card $C_i$.

The steps which are conducted by the computer K, may also be conducted by a laboratory technician, but at substantially lesser degree of automation.

This invention is intended to cover all changes and modifications of the example of the invention herein chosen for purposes of the disclosure which do not constitute departures from the spirit and scope of the invention.

What is claimed is:

1. A process for examining a well containing a culture medium to determine if viable microorganisms exist in the well, a dilution of said culture medium having the capability of undergoing a change in its light transmitting characteristics when a viable microorganism is in the dilution and is sustained by the culture medium, said process comprising: projecting light through the well at successive time intervals, for each time the light is projected detecting the light at a plurality of adjacent locations beyond the well substantially simultaneously to determine the intensity of such light at each location, whereby some locations may register a greater change in light intensity than other locations as the result of bubbles or foreign material affecting the intensity of the light to such locations; and indicating that a viable microorganism is present only when a selected number of locations register a decrease in light intensity in excess of a predetermined value.

2. The process according to claim 1 wherein the well has an optical axis extending from one end of the well to the other, and at least some of the locations at which the light is detected are offset from the optical axis.

3. The process according to claim 2 wherein the locations at which the light is detected are located in a row which extends perpendicular to the optical axis for the well.

4. A process according to claim 1 wherein the ends of the wells are closed by a flexible transparent material capable of assuming a convex configuration which focuses light on the detecting locations at a greater intensity and thereby distorts readings of intensity at such locations, and further comprising adjusting the readings of intensity obtained at the detecting locations so as to compensate for the distortion.

5. The process according to claim 1 wherein the well is in a card having identification segments thereon on which indicia is marked, and further comprising projecting light at the identification segments to read the indicia thereon.

6. The process according to claim 5 wherein the card is transparent and the light which is projected at the identification segment is in several beams with different beams being directed to different portions of the segment, and further comprising sensing the light beams which pass through the card without experiencing a substantial decrease in intensity, thus locating unmarked portions of the identification segment.

7. A process according to claim 6 and further comprising sensing each beam at a plurality of locations with some locations being offset from the axis of the beam.

8. A process according to claim 7 and further comprising indicating the presence of a marking in the segment when the beam projected at that segment registers a predetermined intensity at a selected number of locations at which the beam is monitored.

9. The process according to claim 6 wherein the card contains a plurality of additional wells arranged in succession after the initial well and a plurality of identification segments located in succession; and further comprising moving the card such that the successive wells come into alignment with the light which is directed to the initial well and such that successive identification segments come into alignment with the several beams of light.

10. A machine for examining a card containing a well having a culture medium therein and into which a water specimen is introduced, all for the purpose of detecting metabolic activity of microorganisms which may be in the specimen, said machine comprising: a reading head capable of supporting the card, a first light emitter mounted on the reading head opposite one surface of the card such that the light emitted thereby is projected through the well, a plurality of first light detectors mounted on the reading head adjacent to each other and being directed toward the opposite surface of the card, the detectors being aligned with the light emitter so as to be illuminated by the emitter unless obstructed and each providing a signal which is proportional to the intensity of light cast upon it, the signals from the plurality of detectors being concurrent in time, whereby, when the card is moved to a position in which the well aligns with the emitter and detectors, the detectors will provide simultaneous signals reflecting the intensity of the light passing through the well.

11. A machine according to claim 10 wherein at least some of the detectors are offset to the side of the axis for the well so as to enable light which passes by a bubble within the well to illuminate the offset detectors.

12. A machine according to claim 10 and further comprising a plurality of second light emitters mounted on the reading head and positioned to align with the different bars of an identification segment on the card and light sensors located opposite the second light emitters, there being a separate light sensor for each second light emitter, whereby the sensors aligned with bars having indicia marked thereon will register light of lower intensity than the sensors aligned with bars having no marking on them.

13. A machine according to claim 12 wherein each light sensor comprises a plurality of light detectors, each of which is illuminated by the second light emitter with which the sensor is aligned, whereby stray markings or foreign material on a bar are not likely to reduce the intensity of light cast on all of the detectors for the sensor.

14. A machine according to claim 12 wherein the second emitters and second detectors are arranged in the pattern of the Arabic numeral eight.

15. A machine according to claim 12 and further comprising a cover located in front of the sensors, the cover having transparent windows positioned therein so as to enable the second emitters to illuminate their corresponding sensors.

16. A machine according to claim 12 and further comprising a holder located opposite the supporting element being capable of holding a plurality of cards in succession, and means for withdrawing the cards individually from the holder and moving them to positions on the supporting element with their wells aligned with the first emitter and with their identification segments aligned with the second emitters.

17. A process for examining a card having at least one well that contains a culture medium, the card being capable of receiving a liquid specimen, and the culture medium being selective as to a specific microorganism in the sense that the light transmitting characteristics of the well change when the specific microorganism metabolizes in the well; said process comprising: positioning the card such that its well is between an array of closely spaced light detectors and a light emitter positioned such that unless otherwise obstructed it will illuminate all of the detectors of the array, each detector providing an electrical signal that is proportional to the intensity of the light cast upon it; at successive time intervals projecting a beam of light from the emitter through the well, whereby each of the detectors will provide a signal; for each time the light is projected analyzing the signals substantially contemporaneously; and indicating that a viable microorganism exists in the well only when a selected number of the signals register a decrease in light intensity beyond a predetermined value.

18. The process according to claim 17 wherein the detectors of the array are arranged in a row that extends transversely with respect to the beam of light from the emitter.

19. The process according to claim 17 wherein the ends of the wells are covered by a flexible transparent material that tends to bow outwardly into a convex configuration when the specimen is heated, so as to create a lens that increases the intensity of the light cast on the detectors; and further comprising converting the signals into readings, and adjusting the readings to compensate for the increase in light intensity caused by the tendency of the flexible material to assume a convex configuration.

20. The process according to claim 17 and further comprising converting the signal from only the detector which registers the lowest reduction in light intensity into a reading.

21. The process according to claim 17 and further comprising projecting the light through the well at periodic intervals and recording the readings derived from each time the light is projected.

22. A process for examining a card having at least one well therein and a flexible transparent material covering and closing the end of the well, the well containing a culture medium which is mixed with a water specimen that is introduced into the card, the culture medium causing the light-transmitting capabilities of the specimen-medium mixture to diminish when a microorganism to which the culture medium is sensitive is introduced into the well with the decrease not occurring to any significant extent until after a span of time has elapsed, the flexible transparent material tending to bulge outwardly and create a lens as the microorganism metabolizes in the well, said process comprising: projecting a beam of light through the well after successive intervals of time with the initial interval being less than said span of time so that at least one reading occurs within said span of time; detecting each beam of light beyond the well and providing a reading that corresponds to the intensity of the beam after it passes through the well; and adjusting those readings that are derived after the span of time so as to compensate for any change in intensity caused by the distortion of the flexible transparent material into a lens, whereby those readings reflect the actual decrease in light transmitting characteristics of the well.

23. The process according to claim 22 wherein the distortion of the flexible transparent material causes an increase in intensity of the beam of light when it is detected, and the readings are adjusted to compensate for the increase.

24. The process according to claim 23 wherein intervals are short enough to enable the beam to be projected through the well a plurality of times during said span of time.

25. The process according to claim 22 wherein the intervals after which the beam is projected are periodic and of lesser duration than the span of time.

* * * * *

UNITED STATES PATENT AND TRADEMARK OFFICE
CERTIFICATE OF CORRECTION

PATENT NO. : 4,116,775
DATED : Sep. 26, 1978
INVENTOR(S) : Charles et al.

It is certified that error appears in the above-identified patent and that said Letters Patent are hereby corrected as shown below:

column 1, line 37, after "1974," and before "discloses" insert --- now U. S. Patent 3,957,583 ---.

column 4, line 8, after "characteristics" and before "machine" insert ---of a particular rehydrated media have occured.
<u>The Cards</u>
Two general types of cards are handled by the analyzing ---.

column 8, line 68, after "switch" and before "comes" insert --- 108 ---.

Signed and Sealed this

Sixth Day of March 1979

[SEAL]

Attest:

RUTH C. MASON
Attesting Officer

DONALD W. BANNER
Commissioner of Patents and Trademarks